United States Patent [19]

Shoesmith, deceased

[11] Patent Number: Plant 5,985

[45] Date of Patent: May 12, 1987

[54] CHRYSANTHEMUM PLANT NAMED PRIM

[75] Inventor: Leonard H. Shoesmith, deceased, late of Westfield, United Kingdom, by May V. Shoesmith, executrix

[73] Assignee: Ball Pan Am Plant Company, Parrish, Fla.

[21] Appl. No.: 712,697

[22] Filed: Mar. 18, 1985

[51] Int. Cl.[4] ..... A01H 5/00

[52] U.S. Cl. ..... Plt./76

[58] Field of Search ..... Plt./76, 77

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Chrysanthemum named Prim having a dwarf habit, flat capitulum form and decorative capitulum type, light yellow to white color, eight week response, and an ability to be grown year around in 9 cm. pots with little growth regulation.

1 Drawing Figure

The present invention comprises a new and distinct cultivar of *Chrysanthemum morifolium,* Ramat., hereinafter referred to by the cultivar name Prim.

Prim is a product of a planned breeding program which had the objective of creating new Chrysanthemum cultivars with eight (8) week response, white decorative type flowers, and dwarf habit suitable for year around growing in 9 cm. pots. Such traits in combination were not present in previously available commercial cultivars.

Prim was originated from a hybridization made by Leonard H. Shoesmith in a controlled breeding program in Westfield, Woking, England in 1979. The male and female parents are unknown at this time. Prim was discovered and selected as one flowering plant within the progeny of the parentage by applicant in November, 1980 in a controlled environment in West Chicago, Ill., and given the code name F0-2024-WS.

The first act of asexual reproduction of Prim was accomplished when vegetative cuttings were taken from the initial selection in February, 1981 in a controlled environment in West Chicago, Ill. by a technician working under formulations established and supervised by Leonard H. Shoesmith. Horticultural examination of selected units initiated in March, 1981 has demonstrated that the combination of characteristics as herein disclosed for Prim are firmly fixed and are retained through successive generations of asexual reproduction.

Prim has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Prim, which in combination distinguish this chrysanthemum as a new and distinct cultivar:

1. Flat capitulum form.
2. Decorative capitulum type.
3. Very light flower color in center, with ray florets being white at periphery.
4. Dwarf habit extending 10–15 cm. above edge of pot.

5. Eight (8) week response.
6. Ability to be grown year around in 9 cm. pots in most areas, and requiring few B-9 treatments.

Of the many commercial cultivars known to the present inventor, the most similar in comparison to Prim is the cultivar Surf, disclosed in U.S. Plant Pat. No. 4,585. In comparison to Surf, Prim has smaller flowers of less substance, requires one (1) week less crop time, is more dwarf and therefore more suitable for year around production in 9 cm. pots, and has creamy white flowers. The flower form and type of Prim are similar to those same characteristics of Surf.

The accompanying photographic drawing shows typical inflorescence characteristics of Prim, with colors being as nearly true as possible with illustrations of this type. The photograph is in black and white, with a single flower being colored to accurately depict true flower color.

In the following description color references are made to The Royal Horticultural Society Colour Chart. The color values were determined at approximately 11:00 a.m. on Jan. 17, 1985 under natural and fluorescent light at Bradenton, Fla.

Classification:

*Botanical.*—*Chrysanthemum morifolium,* Ramat., CV Prim.

*Commercial.*—Decorative spray, four (4) inch pot.

I. INFLORESCENCE

A. Capitulum:

*Form.*—Flat.

*Type.*—Decorative.

*Diameter across face.*—3–5 cm.

B. Corolla of ray florets:

*Color (general tonality from a distance of three meters).*—Light yellow (center) to white.

*Color (under surface).*—2 D.

*Color (top surface).*—4 D in center, white 155D near and at periphery.

C. Corolla of disc florets:

*Color (mature).*—Light yellow.

*Color (immature).*—Light yellow.

D. Reproductive organs:

*Androecium.*—Present in disc florets only; few in number.

*Gynoecium.*—Present in both ray and disc florets; numerous.

II. PLANT

A. General appearance:

*Height.*—10–15 cm. above edge of pot when properly grown in 9 cm. pot.

B. Foliage:

*Color* (*under surface*).—147 B.

*Color* (*top surface*).—147 A.

*Shape.*—Ovate and deeply lobed.

It is claimed:

1. A new and distinct cultivar of Chrysanthemum named Prim, as described and illustrated, and particularly characterized by its dwarf habit; flat capitulum form and decorative capitulum type; light yellow to white color; eight week response, and by its ability to be grown year around in 9 cm. pots with little growth regulation.

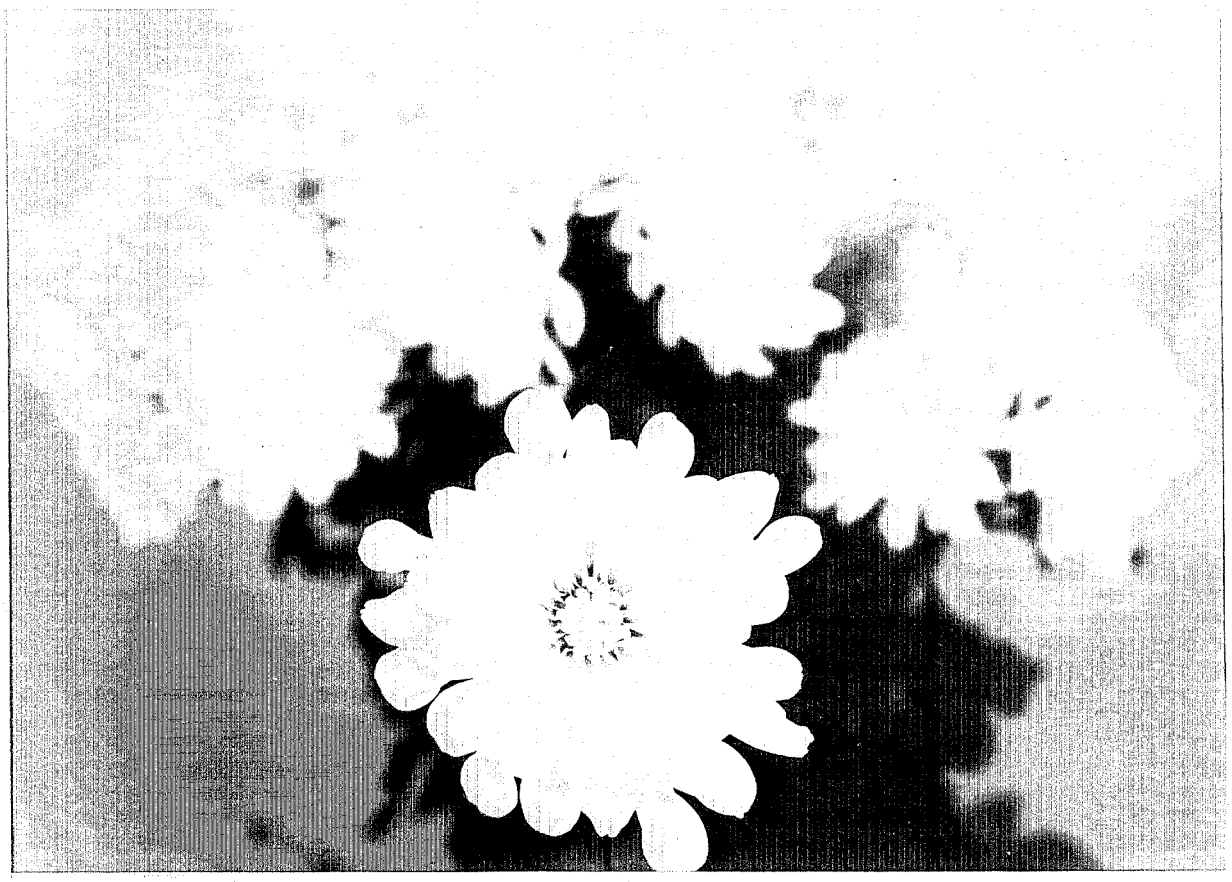

* * * * *